US009250544B2

(12) United States Patent
Kim et al.

(10) Patent No.: US 9,250,544 B2
(45) Date of Patent: Feb. 2, 2016

(54) PARTICLE COUNTER AND IMMERSION EXPOSURE SYSTEM INCLUDING THE SAME

(71) Applicant: Samsung Electronics Co., Ltd., Suwon-Si, Gyeonggi-Do (KR)

(72) Inventors: Jinho Kim, Hwaseong-si (KR); Jiyoung Kim, Suwon-si (KR); Jeong-In Yoon, Hwaseong-si (KR); Kwangshin Lim, Yongin-si (KR)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 159 days.

(21) Appl. No.: 14/080,977

(22) Filed: Nov. 15, 2013

(65) Prior Publication Data
US 2014/0268079 A1    Sep. 18, 2014

(30) Foreign Application Priority Data

Mar. 15, 2013    (KR) .......................... 10-2013-0028114

(51) Int. Cl.
*G03B 27/54*    (2006.01)
*G03F 7/20*    (2006.01)
*G01N 15/00*    (2006.01)
*G01N 15/14*    (2006.01)

(52) U.S. Cl.
CPC .............. *G03F 7/7085* (2013.01); *G01N 15/00* (2013.01); *G01N 15/1434* (2013.01); *G01N 15/1459* (2013.01); *G03F 7/70341* (2013.01); *G03F 7/70916* (2013.01); *G01N 2015/0011* (2013.01); *G01N 2015/0053* (2013.01)

(58) Field of Classification Search
CPC .............. G01N 15/00; G01N 15/1434; G01N 15/1459; G01N 2015/0011; G01N 2015/0053; G03F 7/70341; G03F 7/7085; G03F 7/70916
USPC .......................................................... 355/30
See application file for complete search history.

(56) References Cited

U.S. PATENT DOCUMENTS

| 4,488,248 A | 12/1984 | Okada et al. |
| 4,761,074 A | 8/1988 | Kohsaka et al. |
| 5,583,635 A | 12/1996 | Miura et al. |
| 6,534,743 B2 | 3/2003 | Swenson et al. |
| 7,601,976 B2 | 10/2009 | Hill et al. |
| 7,777,868 B2 | 8/2010 | Blackford et al. |
| 7,852,476 B2 | 12/2010 | Moriya |

(Continued)

FOREIGN PATENT DOCUMENTS

| JP | 64-065434 B2 | 3/1989 |
| JP | 09-054034 A | 2/1997 |

(Continued)

*Primary Examiner* — Peter B Kim
(74) *Attorney, Agent, or Firm* — Harness, Dickey & Pierce, P.L.C.

(57) ABSTRACT

A particle counter may include a housing having an inlet, an outlet, and a window therebetween. The inlet and the outlet may be configured such that a fluid can be flowed therethrough. A plurality of light sources may be arranged outside the housing to provide lights of different wavelengths into the housing through the window. Sensors may be provided outside the housing to detect fractions of the lights scattered by a bubble and/or a particle in the fluid. A control part may be configured to monitor intensities of the lights detected by the sensors and to analyze a difference in intensity between the scattered lights, thereby distinguishing the particles from the bubbles in the fluid.

19 Claims, 5 Drawing Sheets

(56) References Cited

U.S. PATENT DOCUMENTS

| | | |
|---|---|---|
| 8,030,082 B2 | 10/2011 | Strothers et al. |
| 8,981,298 B2 * | 3/2015 | Wagner et al. ............ 250/339.07 |
| 2005/0024609 A1 * | 2/2005 | De Smit et al. ................ 355/18 |
| 2005/0078286 A1 * | 4/2005 | Dierichs et al. ................ 355/30 |
| 2005/0175508 A1 | 8/2005 | Hill |
| 2012/0008143 A1 | 1/2012 | Ihlefeld et al. |

FOREIGN PATENT DOCUMENTS

| | | |
|---|---|---|
| JP | 2003-279484 A | 10/2003 |
| JP | 4026191 B2 | 12/2007 |
| KR | 2005-0014424 A | 2/2005 |
| KR | 10-0499164 B1 | 6/2005 |
| KR | 2006-0014003 A | 2/2006 |
| KR | 2009-0120121 A | 11/2009 |

* cited by examiner

PARTICLE COUNTER AND IMMERSION EXPOSURE SYSTEM INCLUDING THE SAME

CROSS-REFERENCE TO RELATED APPLICATION

This U.S. non-provisional patent application claims priority under 35 U.S.C. §119 to Korean Patent Application No. 10-2013-0028114, filed on Mar. 15, 2013 in the Korean Intellectual Property Office, the entire contents of which are hereby incorporated by reference.

BACKGROUND

Example embodiments of the present disclosure relate to a particle counting device and/or an exposure system with the same, and in particular, to a particle counter configured to distinguish particles from bubbles in fluid and/or an immersion exposure system having the same.

Conventionally, the formation of a semiconductor device includes a plurality of unit processes, such as a thin-film deposition process, a photolithography process, and an etching process. To form a photoresist pattern serving as an etch mask on a wafer or a thin layer, the photolithography process includes a photoresist coating process, an exposure process, and a developing process. The exposure process is performed to selectively expose a photoresist layer with ultraviolet light using a photomask or a reticle, and the developing process is performed to selectively remove one of exposed or non-exposed portions of the photoresist layer.

A critical dimension (CD) of a semiconductor device may be decided by an exposure system to be used for the exposure process. A density of the semiconductor device may be inversely proportional to a wavelength of an exposure light to be used in the exposure process. In the past, a G- or I-line had been used for the exposure light, but KrF or ArF is recently being used for the exposure light. Although the ArF light has the minimum wavelength that can be achieved from the commercialized light sources for the exposure process, the usage of an immersion exposure system makes it possible to use an ultraviolet light, whose wavelength is shorter than that of the ArF light. In the immersion exposure system, the water, whose refractive index is higher than that of the air, is interposed between an object lens and a wafer of ArF exposure system, and thus, a light with shorter wavelength can be used for the exposure process.

SUMMARY

Some example embodiments of the present disclosure relate to a particle counter configured to distinguish particles from bubbles in a fluid and an immersion exposure system including the same.

Some example embodiments of the present disclosure relate to a particle counter configured to be able to increase a production yield of a photolithography process and an immersion exposure system including the same.

According to example embodiments of the present disclosure, a particle counter may include a housing having an inlet, an outlet, and a window, the inlet and the outlet being configured in such a way that a fluid can be flowed therethrough, the window disposed between the inlet and the outlet, a plurality of light sources provided outside the housing to provide lights, whose wavelengths are different from each other, sensors provided outside the housing to detect fractions of the lights scattered by a bubble and/or a particle in the fluid, and a control part configured to monitor intensities of the lights detected by the sensors and analyze a difference in intensities of the scattered lights of the particles and/or bubbles in the fluid.

In example embodiments, the plurality of the light sources may include a first laser and a second laser, each of which may be configured to emit a laser light having the single wavelength. The first laser and the second laser may be configured to generate first and second laser lights, respectively, which have the same intensity and may be incident into the fluid.

In example embodiments, the control part is configured to distinguish between the particle having a varying refractive index and the bubble having a constant refractive index.

In example embodiments, the light sources and the sensors may be provided on a plane normal to a flowing direction of the fluid in the housing. Here, the light sources and the sensors may be disposed in such a way that an angle therebetween is about 90 degrees with respect to a center of the housing.

In example embodiments, the housing may further include a mirror, the mirror and the window disposed to face each other.

In example embodiments, the control part may be configured to produce pulses of control signal that may be used to control operations of the light sources and the sensors.

According to example embodiments of the present disclosure, an immersion exposure system may include a stage configured to support a wafer coated with a photoresist, an exposing part comprising an object lens configured to allow ultraviolet light to be incident upon the photoresist on the wafer, a guard enclosing a space between the object lens and the wafer, a fluid supplying part configured to supply a fluid into the guard, and a fluid drain part configured to exhaust the fluid from the guard. The fluid drain part may include a particle counter including a housing having an inlet, an outlet, and a window, the inlet and the outlet being configured in such a way that a fluid can be flowed therethrough, the window disposed between the inlet and the outlet, a plurality of light sources provided outside the housing to provide lights, whose wavelengths are different from each other, sensors provided outside the housing to detect fractions of the lights scattered by a bubble and/or a particle in the fluid, and a control part configured to monitor intensities of the lights detected by the sensors and to analyze a difference in intensities of the scattered lights of the particle and/or bubble in the fluid.

In example embodiments, the fluid drain part may further include a fluid exhauster, an exhausting conduit between the fluid exhauster and the guard, and an exhausting valves configured to control flows of the fluid passing through the exhausting conduit. The exhausting conduit may include a main exhausting conduit connected to the guard, a first branch exhausting conduit branching off from the main exhausting conduit and being directly connected to the fluid exhauster, and a second branch exhausting conduit provided to connect the main exhausting conduit to the particle counter and to connect the particle counter to the fluid exhauster. The exhausting valves may include a first exhausting valve provided on the first branch exhausting conduit, and a second exhausting conduit provided on the second branch exhausting conduit.

In example embodiments, the fluid supplying part may include a fluid source, a supplying conduit connecting the fluid source to the guard, and a supplying valve configured to control flows of the fluid passing through the supplying conduit.

In example embodiments, the immersion exposure system may further include a system control part configured to output an interlock control signal when the particle in the fluid is detected by the particle counter.

In other example embodiments a particle counter may include a housing including an inlet, an outlet, and a window between the inlet and the outlet, the housing configured to transport a fluid therethrough from the inlet to the outlet; light sources arranged outside the window of the housing, the light sources configured to illuminate the fluid with lights of different wavelengths; sensors arranged within optical communication with the light sources, the sensors configured to detect reflections of the lights scattered by at least one of bubbles and particles in the fluid; and a control part configured to analyze a difference in intensities of the reflections of the lights. The housing may further include a mirror that faces the window. The mirror may be curved, and a concave portion of the mirror may face the window. The light sources may be configured such that the lights are incident upon the fluid with a same intensity. The light sources and the sensors may be aligned such that an illumination direction of the light sources is orthogonal to a detection direction of the sensors.

BRIEF DESCRIPTION OF THE DRAWINGS

Example embodiments may be more clearly understood when the following description is taken in conjunction with the accompanying drawings. The accompanying drawings represent non-limiting, example embodiments as described herein.

Figure 1:
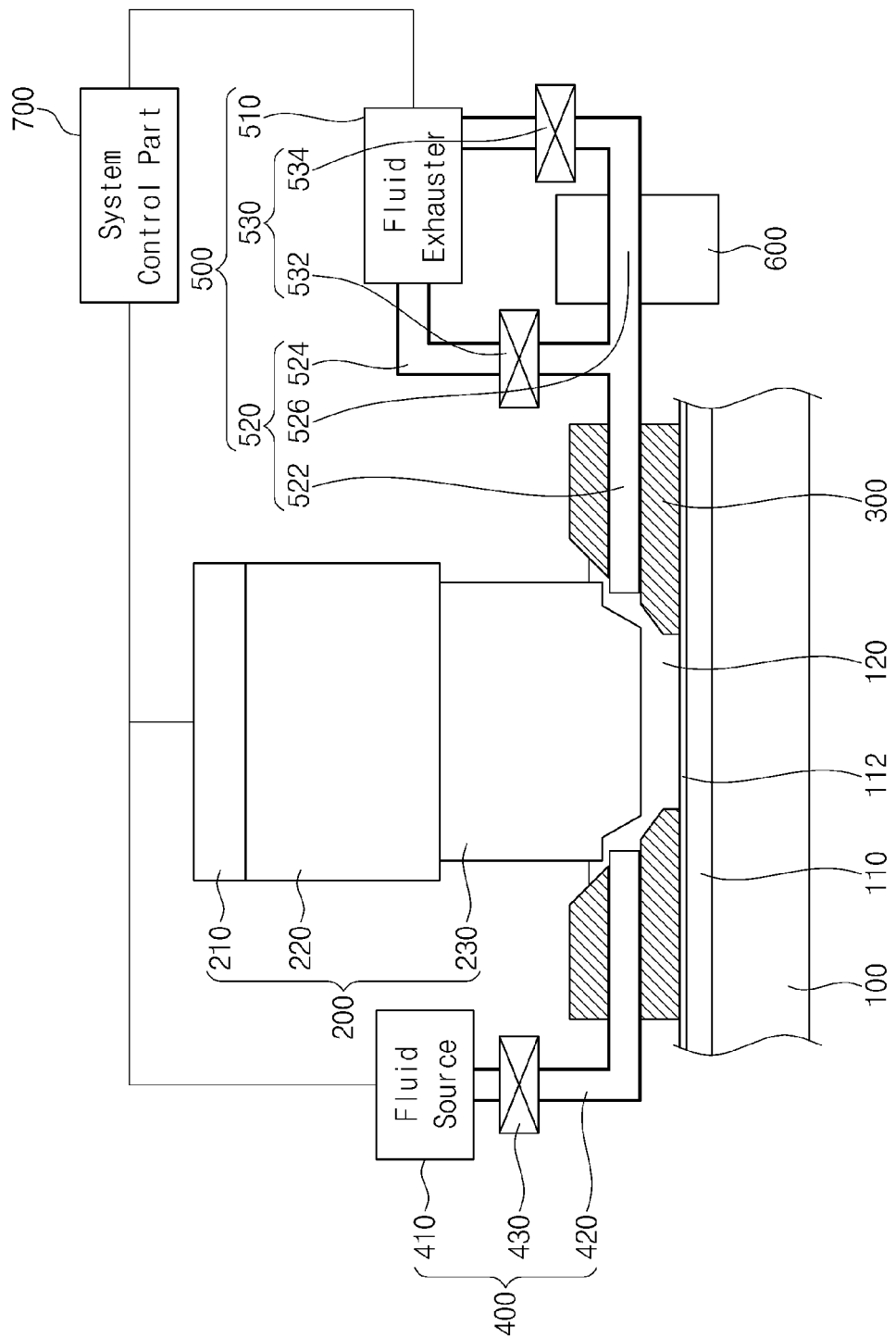
FIG. 1 is a schematic diagram illustrating an exposure system according to example embodiments of the present disclosure.

It should be noted that these figures are merely intended to illustrate the general characteristics of methods, structure and/or materials utilized in certain example embodiments and to supplement the written description provided below. These drawings, however, may not be to scale and may not precisely reflect the precise structural or performance characteristics of any given embodiment, and should not be interpreted as defining or limiting the range of values or properties encompassed by example embodiments. For example, the relative thicknesses and positioning of molecules, layers, regions and/or structural elements may have been reduced or exaggerated for clarity. The use of similar or identical reference numbers in the various drawings is intended to indicate the presence of a similar or identical element or feature.

DETAILED DESCRIPTION

Example embodiments of the present disclosure will now be described more fully with reference to the accompanying drawings, in which example embodiments are shown. Example embodiments of the present disclosure may, however, be embodied in many different forms and should not be construed as being limited to the embodiments set forth herein. Rather, these embodiments are provided so that this disclosure will be thorough and complete, and will fully convey the concept of example embodiments to those of ordinary skill in the art. In the drawings, the thicknesses of layers and regions may have been exaggerated for clarity. Like reference numerals in the drawings denote like elements, and thus their description will be omitted.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Like numbers indicate like elements throughout. As used herein the term "and/or" includes any and all combinations of one or more of the associated listed items. Other words used to describe the relationship between elements or layers should be interpreted in a like fashion (e.g., "between" versus "directly between," "adjacent" versus "directly adjacent," "on" versus "directly on").

It will be understood that, although the terms "first", "second", etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of example embodiments.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises", "comprising", "includes" and/or "including," if used herein, specify the presence of stated features, integers, steps, operations, elements and/or components, but do not preclude the presence or addition of one or more other features, integers, steps, operations, elements, components and/or groups thereof.

Unless otherwise defined, all terms (including technical and scientific terms) used herein have the same meaning as commonly understood by one of ordinary skill in the art to which example embodiments of the present disclosure belong. It will be further understood that terms, such as those defined in commonly-used dictionaries, should be interpreted as having a meaning that is consistent with their meaning in the context of the relevant art and will not be interpreted in an idealized or overly formal sense unless expressly so defined herein.

FIG. 1 is a schematic diagram illustrating an exposure system according to example embodiments of the present disclosure.

Referring to FIG. 1, the immersion exposure system according to example embodiments of the present disclosure may include a stage 100, an exposing part 200, a guard 300, a fluid supplying part 400, a fluid drain part 500, a particle counter 600, and a system control part 700.

The stage 100 may be configured to support and/or move horizontally a wafer 110. The wafer 110 may be coated with a photoresist 112. The photoresist 112 may include a material having a photo-sensitivity with respect to ultraviolet light, which may be transmitted from the exposing part 200.

The exposing part 200 may be configured to expose ultraviolet light to the photoresist 112 using a reticle 240 as a mask pattern (not shown). The exposing part 200 may include an ultraviolet light source 210, a collimator 220, and an object lens 230. The ultraviolet light source 210 may be configured to generate ultraviolet light (e.g., KrF (234 nm) light or ArF (193 nm) light. The collimator 220 may be configured to collimate the ultraviolet light generated from the ultraviolet light source 210. The collimated light may be transmitted to the reticle 240. In example embodiments, the collimator 220 may include a dipole or quadruple aperture, thereby increasing a focal depth of the ultraviolet light. The object lens 230 may be configured to focus the ultraviolet light on the wafer 110. In example embodiments, a diameter of the object lens 230 may determine a size of a shot realized by the exposing part 200. For example, the object lens 230 may be configured in such a way that the size of the shot is about one fourth of a mask image of the reticle 240.

Although not shown, a plurality of optical components, such as lens or mirror, may be further provided between the collimator 220 and the object lens 230. In addition, at least one optical component may be further provided between the ultraviolet light source 210 and the object lens 230.

The guard 300 may be configured to confine fluid 120 between the object lens 230 of the exposing part 200 and the wafer 110. The fluid 120 may be water having a higher refractive index than air. For example, the air may have a refractive index of about 1, while the water may have a refractive index of about 1.44. The guard 300 may be shaped like a ring, whose diameter is larger than that of the object lens 230. In example embodiments, the water may be re-filled in the guard 300, during or after the exposure process, because the water could be heated and vaporized.

The fluid supplying part 400 may include a fluid source 410, a supplying conduit 420, and a supplying valve 430. The supplying conduit 420 may be connected to a portion of the guard 300. The fluid source 410 may be configured to supply the fluid into the guard 300. The fluid source 410 may include a water pump. The supplying valve 430 may be configured to control the supply of the fluid 120. The supplying valve 430 may be connected to the supplying conduit 420.

Figure 2:
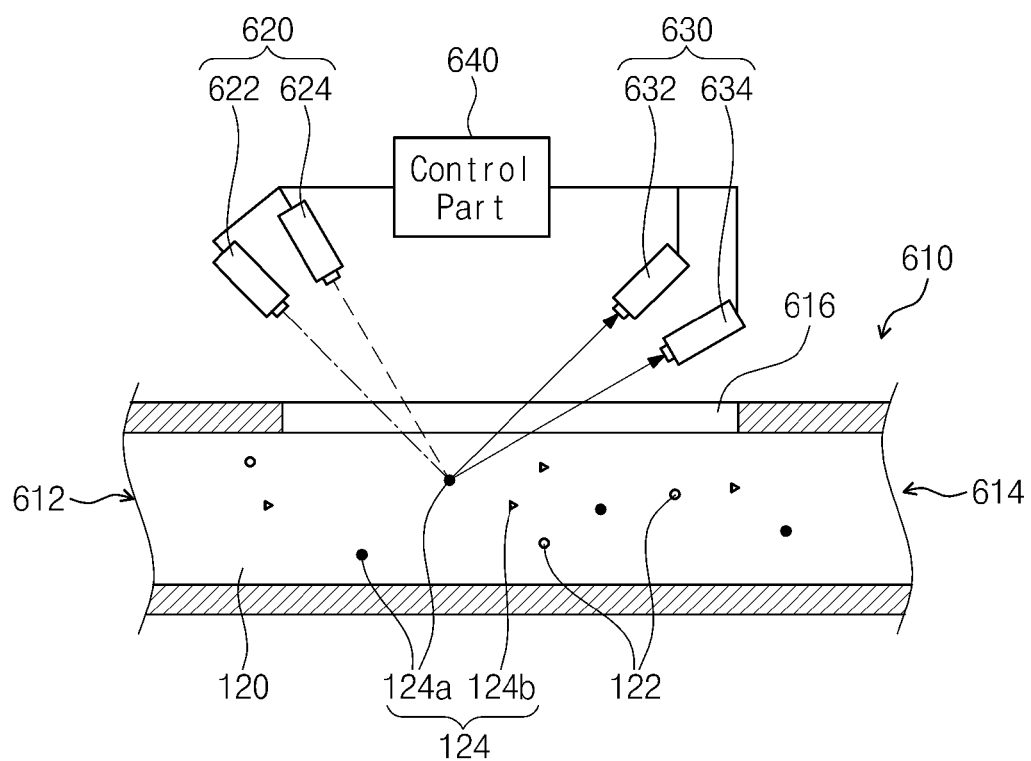
FIG. 2 is a schematic diagram illustrating a particle counter of FIG. 1.

The fluid drain part 500 may include a fluid exhauster 510, an exhausting conduit 520, and at least one exhausting valve 530. The fluid exhauster 510 may include a water pump. The exhausting conduit 520 may include a main exhausting conduit 522, a first branch exhausting conduit 524, and a second branch exhausting conduit 526. The main exhausting conduit 522 may be connected to the guard 300. The first branch exhausting conduit 524 and the second branch exhausting conduit 526 may branch off from the main exhausting conduit 522. The first branch exhausting conduit 524 may be configured to connect the main exhausting conduit 522 directly to the fluid exhauster 510. The at least one exhausting valve 530 may include first and second exhausting valves 532 and 534, which are configured to control flows of the fluid 120 passing through the first and second branch exhausting conduits 524 and 526, respectively. The second branch exhausting conduit 526 may extend from the main exhausting conduit 522 to the fluid exhauster 510 through the particle counter 600. The particle counter 600 may be configured to count the number of particles (e.g., 124 of FIG. 2), which may be contained in the fluid 120 flowing through the second branch exhausting conduit 526. As shown in FIG. 2, the particles 124 may include a particle originated from a photoresist (hereinafter, referred as to a photoresist particle 124a) or a particle produced from an anti-reflecting layer (hereinafter, referred as to an anti-reflecting particle 124b). In example embodiments, the particle counter 600 may be configured to detect and distinguish a bubble 122 and the particle 124 in the fluid 120.

The system control part 700 may be configured to produce and output control signals for controlling the stage 100, the exposing part 200, the fluid supplying part 400, and the fluid drain part 500. The particle counter 600 may be configured to provide a particle detection signal to the system control part 700. When the system control part 700 receives the particle detection signal form the particle counter 600, it may output an interlock control signal in order to prevent the exposure process from being failed or rendered unsatisfactory by the particle 124 in the fluid 120. This makes it possible to improve a production yield of the exposure system.

FIG. 2 is a schematic diagram illustrating the particle counter 600 of FIG. 1.

Referring to FIG. 2, according to example embodiments of the present disclosure, the particle counter 600 may include a housing 610, at least one visible light source 620, at least one sensor 630, and a control part 640. The housing 610 may be connected to the second branch exhausting conduit 526. The housing 610 may be configured to have an inlet 612, an outlet 614, and a window 616. The inlet 612 and the outlet 614 may be connected to the second branch exhausting conduit 526. The window 616 may include a transparent material, such as glass or plastic. In other words, the window 616 may be configured to allow a visible light (e.g., first and second laser lights) to transmit through the housing 610 and be incident into the fluid 120.

The visible light sources 620 may include a first laser light source 622 and a second laser light source 624. The first laser light source 622 may be configured to produce a first laser light having a wavelength of about 400 nm, although example embodiments are not limited thereto. The second laser light source 624 may be configured to produce a second laser light having a wavelength of about 700 nm, although example embodiments are not limited thereto. In example embodiments, the first and second laser light sources 622 and 624 may be configured in such a way that the first and second laser lights can be incident into the fluid 120 with substantially the same intensity.

The first laser light and the second laser light may transmit through the window 616 and the fluid 120. An inner wall of the housing 610 facing the window 616 may be configured to absorb the first and second laser lights. The first and second laser lights may be scattered by the bubbles 122 and/or the particles 124, which may exist in the fluid 120. The scattered light may be detected by the sensors 630. In example embodiments, the sensors 630 may include a first sensor 632 and a second sensor 634. The first sensor 632 may be configured to detect the first laser light scattered by the bubbles 122 and/or the particles 124. The second sensor 634 may be configured to detect the scattered second laser light.

The control part 640 may be configured to distinguish the bubbles 122 from the particles 124 based on a difference in intensity between the first and second laser lights. When the first and second laser lights are scattered by the bubbles 122 and the particles 124, the signal intensities of the scattered first and second laser lights may be given by the following Rayleigh scattering equation:

[Rayleigh scattering equation]

$$I = I_0 \left(\frac{1+\cos^2\theta}{2R^2}\right)\left(\frac{2\pi}{\lambda}\right)^4 \left(\frac{n^2-1}{n^2+2}\right)^2 \left(\frac{d}{2}\right)^6,$$

where I is an intensity of a scattered light, $I_0$ is an intensity of an incident light (e.g., from each of the first and second laser light sources 622 and 624), θ is a scattering angle, R is a distance between the particle and the sensor, and d is a diameter of the particle. The angular distribution of Rayleigh scattering, governed by the term of $(1+\cos^2\theta)$, may be symmetric in the normal plane to the incident direction of the light. Accordingly, the intensity of the scattered light may have strong dependency on a wavelength of the scattered light and a refractive index of a material, such as air or a particle.

Figure 3:
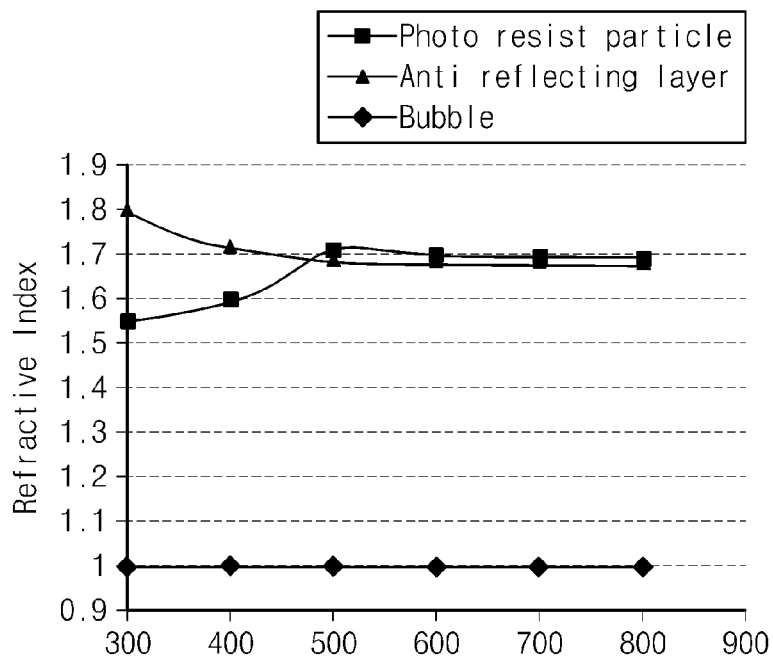
FIG. 3 is a graph showing refractive indices of a bubble, a photoresist particle, and an anti-reflecting layer, which were measured over the wavelength range of visible light.

FIG. 3 is a graph showing refractive indices of the bubble 122, the particle 124a of the photoresist 112, and the particle 124b of the anti-reflecting layer, which were measured over the wavelength range of visible light.

Referring to FIGS. 1 through 3, when a wavelength of the incident light was changed, a refractive index of the bubble 122 was substantially constant, but a refractive index of the particle 124 was changed depending on the wavelength of the incident light. For example, the bubble 122 may have a constant refractive index of about 1, regardless of the wavelength of the incident visible light. By contrast, the refractive index of the particle 124a from the photoresist 112 may be about 1.73 for the first laser light of a relatively short wavelength and about 1.68 for the second laser light of a relatively long wavelength. The refractive index of the particle 124b from the anti-reflecting layer may be about 1.60 for the first laser light and about 1.69 for the second laser light. The refractive index of the water may be about 1.44. According to the Rayleigh scattering equation, intensities of the first and second laser lights are inversely proportional to the biquadratic of the wavelength of the visible light. This difference in refractive index and scattered light intensity between the bubble 122 and the particle 124 allows for the control part 640 to distinguish the particle 124 from the bubble 122.

When the first and second laser lights are scattered by the bubble 122 and the particle 124 in the fluid 120, the wavelengths thereof may not be changed. The intensity of the scattered light may be detected by the first sensor 632 and the second sensor 634. When a difference in intensity of the scattered light is uniform, the control part 640 interprets that there may be bubbles 122 in the fluid 120. In the fluid 120, the bubbles 122 may be produced by a microsieve on the inner wall of the housing 610. If there are only the bubbles 122 in the fluid 120, the system control part 700 may control the system in such a way that a next exposure process is performed without interruption.

When a difference in intensity of the scattered light is changed, the control part 640 interprets that there may be particles 124 in the fluid 120. In order to prevent a process failure from occurring in the photolithography process, an interlock control signal may be generated by the system control part 700. In this case, the operator may examine where the particle 124 is produced in the fluid 120, and, if the problem is solved, the exposure process may be continued.

Accordingly, the use of the particle counter 600 according to example embodiments of the present disclosure makes it possible to increase production yield of the photolithography process.

Figure 4:
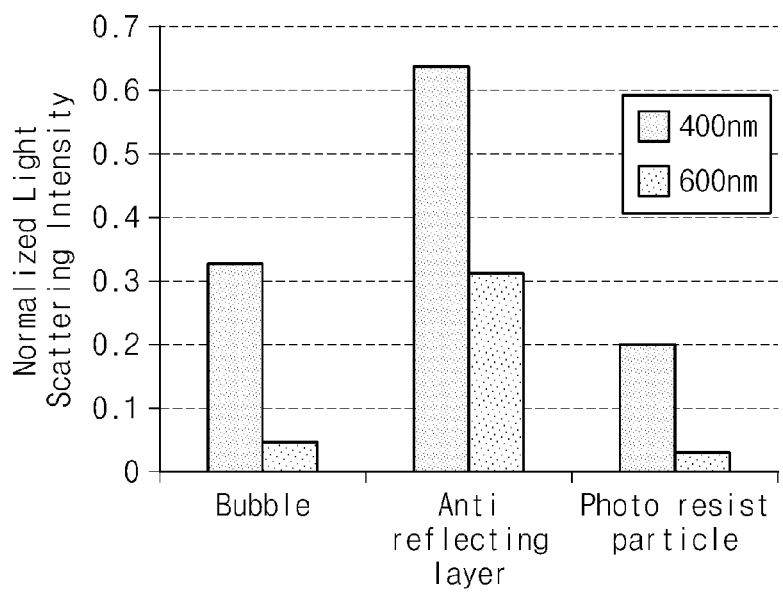
FIG. 4 is a graph showing intensities of normalized visible lights scattered by a bubble, an anti-reflecting layer, and a photoresist.

FIG. 4 is a graph showing intensities of normalized visible lights scattered by the bubble 122, the particle 124b of the anti-reflecting layer, and the particle 124a of the photoresist 112.

Referring to FIG. 4, a difference in intensity of the scattered light was about 0.25 for the bubble 122, about 0.34 for the particle 124b of the anti-reflecting layer, and about 0.17 for the particle 124a of the photoresist 112. The control part 640 may be configured to store datum on signal intensity ratio into a data base (not shown), on the basis of refractive index information on contaminants. The control part 640 may be configured to distinguish the bubble 122 from the particle 124 based on the difference in intensity of the scattered lights and classify them. Further, the control part 640 may be configured to determine a composition ingredient of the particle 124. This allows the engineer to examine the origin of the particles with relative ease in addition to the monitoring of a contamination state of the immersion exposure system. In addition, it is possible to examine and solve relatively quickly the origin of system pollution, when a process failure occurs.

Accordingly, the use of the particle counter 600 according to example embodiments of the present disclosure makes it possible to increase production yield of the photolithography process.

Figure 5:
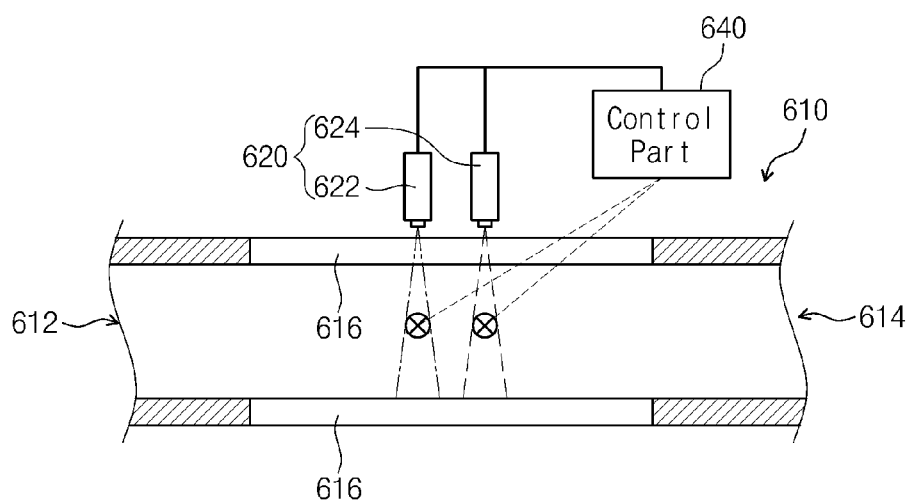
FIGS. 5 through 7 are schematic diagrams showing particle counters according to other example embodiments of the present disclosure.
Figure 6:
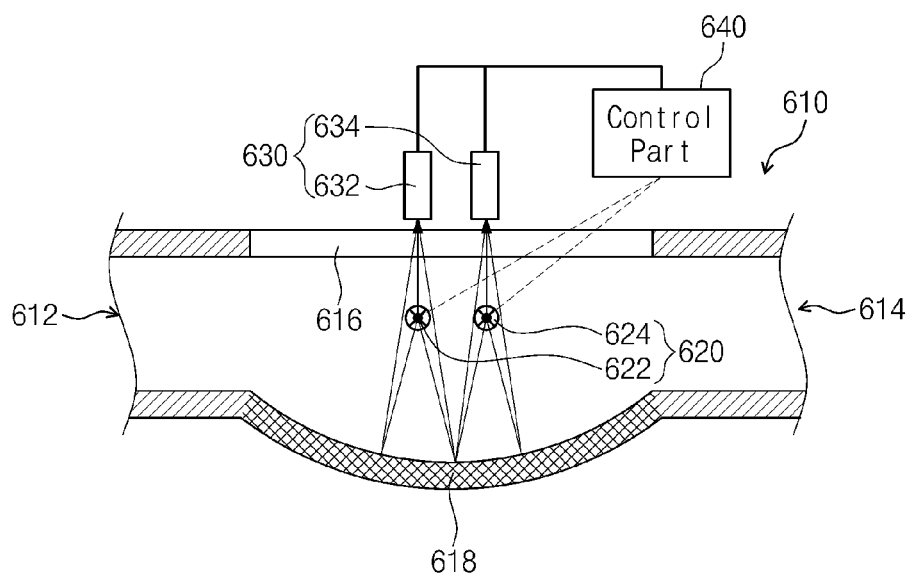
Figure 7:
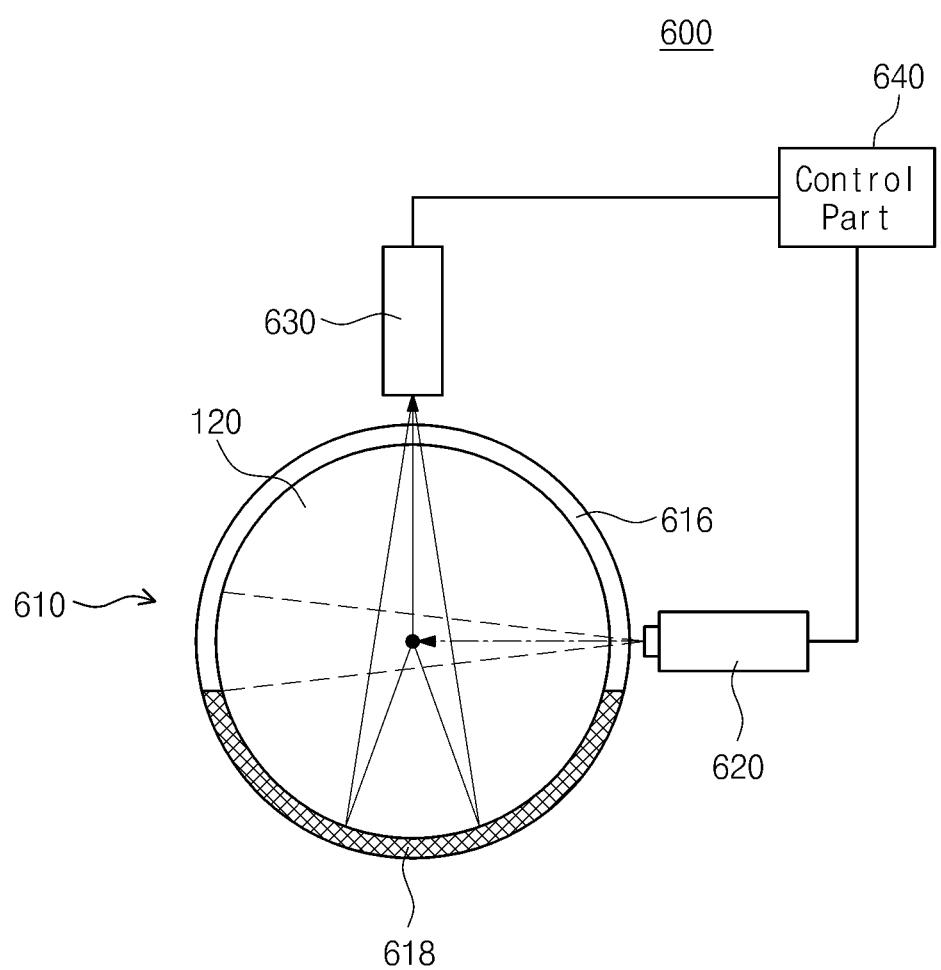

FIGS. 5 through 7 are schematic diagrams showing particle counters according to other example embodiments of the present disclosure.

Referring to FIGS. 1, 2, and 5 through 7, according to other example embodiments of the present disclosure, the particle counter 600 may include a mirror 618. The mirror 618 may reflect the scattered light to the sensors 630. The light sources 620 and the sensors 630 may be provided on a plane normal to a flowing direction of the fluid 120. Further, the light sources 620 and the sensors 630 may be disposed in such a way that an angle therebetween is about 90 degrees with respect to a center of the housing 610. The window 616 may be configured in such a way that the first and second laser lights from light sources 620 can be transmitted through the whole region thereof. Although not shown, in the case where the housing 610 may be configured to have a plurality of the windows 616 facing the light sources 620 and the sensors 630, respectively, and in this case, the first and second laser lights incident into the fluid 120 may be absorbed by the inner wall of the housing 610. The mirror 618 and the window 616 may be provided to face each other. The window 616 may be larger than the mirror 618. The mirror 618 may be shaped like an ellipse elongated along the flowing direction of the fluid 120.

The control part 640 may produce pulses of a control signal, which may be used to control operations of the light sources 620 and the sensors 630. The light sources 620 and the sensors 630 may periodically detect the presence of the bubble 122 and/or the particle 124 in the fluid 120, in response to the pulses of control signal. The light sources 620 and the sensors 630 may be operated in response to the pulses of control signal. For example, the control part 640 may produce turn-on control signals for operating the light sources 620 and the sensors 630 every about 1 or 6 hours. The light sources 620 may be configured to allow the first and second laser lights to be incident into the fluid 120. Fractions of the first and second laser lights may be scattered by the bubble 122 and/or the particle 124. The scattered fraction of the first and second laser lights may be reflected by the mirror 618. The reflected fraction of the first and second laser lights may be transmitted to the sensors 630. The sensors 630 may output detection signals of the first and second laser lights. The control part 640 may be configured to determine and distinguish the bubble 122 and the particle 124 using a difference in intensity between the first and second laser lights. The system control part 700 and the control part 640 may output the same operation and control signals.

Although not shown, according to other example embodiments of the present disclosure, the particle counters 600 may be provided on a latter portion of an air cleaning unit or a water purifier. In this case, even when the particle-induced pollution of air or water may occur in the air cleaning unit or the water purifier, such a use of the particle counter 600 allows engineers to monitor the presence or absence of a failure in the air cleaning unit or the water purifier and analyze the ingredient of a contaminant.

According to example embodiments of the present disclosure, the particle counter may include a housing, a plurality of light sources, a plurality of sensors, and a control part. The housing may include a window allowing laser lights from light sources to be transmitted therethrough. The light sources may include a first laser generating a first laser light with a relatively short wavelength and a second laser generating a second laser light with a relatively long wavelength. The first laser and the second laser may be configured to provide first and second laser lights having the same intensity into the fluid through the window. The sensors may detect fractions of the first and second laser lights scattered by a bubble and/or a particle, which may exist in the fluid. When measured by the first laser light and the second laser lights, the bubble has a constant refractive index and the particle has a varying refractive index. In other words, the bubble and the particle may exhibit different intensity properties, when the scattered fractions of the first and second laser lights may be measured by the sensors. In the control part, the difference in intensity between the first and second laser lights may be used to distinguish the particles from the bubbles in the fluid. Further, the control part may be configured to determine a composition ingredient of the particle. Accordingly, it is possible to examine and solve relatively quickly the origin of system pollution, when a process failure occurs.

Accordingly, the use of the particle counter according to example embodiments of the present disclosure makes it possible to increase production yield of the immersion exposure system.

While example embodiments of the present disclosure have been particularly shown and described, it will be understood by one of ordinary skill in the art that variations in form and detail may be made therein without departing from the spirit and scope of the attached claims.

What is claimed is:

1. A particle counter, comprising:
   a housing having an inlet, an outlet, and a window, the inlet and the outlet configured to transport a fluid through the housing, the window disposed between the inlet and the outlet;
   a plurality of light sources provided outside the housing, the plurality of light sources configured to provide lights with different wavelengths;
   sensors provided outside the housing, the sensors configured to detect fractions of the lights scattered by a bubble or a particle in the fluid; and
   a control part configured to monitor intensities of the fractions of the lights detected by the sensors and to analyze a difference in intensities of the fractions of the lights scattered by the bubble or the particle in the fluid, the control part configured to distinguish between the particle and the bubble, the particle having a varying refractive index, and the bubble having a constant refractive index.

2. The particle counter of claim 1, wherein the plurality of the light sources comprises a first laser and a second laser, each of which is configured to emit a laser light having a single wavelength.

3. The particle counter of claim 2, wherein the first laser and the second laser are configured to respectively generate a first laser light and second laser light of a same intensity.

4. The particle counter of claim 1, wherein the plurality of light sources and the sensors are provided on a plane normal to a flowing direction of the fluid in the housing.

5. The particle counter of claim 4, wherein the plurality of light sources and the sensors are disposed such that an angle therebetween is about 90 degrees with respect to a center of the housing.

6. The particle counter of claim 1, wherein the housing further comprises a mirror, the mirror and the window disposed to face each other.

7. The particle counter of claim 6, wherein the mirror is shaped like an ellipse.

8. The particle counter of claim 1, wherein the control part is configured to produce pulses of a control signal that are used to control operations of the plurality of light sources and the sensors.

9. An immersion exposure system, comprising:
   a stage configured to support a wafer coated with a photoresist;
   an exposing part comprising an object lens, the exposing part configured to allow ultraviolet light to be incident upon the photoresist on the wafer;
   a guard enclosing a space between the object lens and the wafer;
   a fluid supplying part configured to supply a fluid into the guard; and
   a fluid drain part configured to exhaust the fluid from the guard, the fluid drain part including a particle counter, the particle counter including
      a housing having an inlet, an outlet, and a window, the inlet and the outlet configured to transport a fluid through the housing, the window disposed between the inlet and the outlet;
      a plurality of light sources provided outside the housing, the plurality of light sources configured to provide lights with different wavelengths;
      sensors provided outside the housing, the sensors configured to detect fractions of the lights scattered by a bubble or a particle in the fluid; and
      a control part configured to monitor intensities of the fractions of the lights detected by the sensors and to analyze a difference in intensities of the fractions of the lights scattered by the bubble or the particle in the fluid, the control part configured to distinguish between the particle and the bubble, the particle having a varying refractive index, and the bubble having a constant refractive index.

10. The immersion exposure system of claim 9, wherein the fluid drain part further comprises:
   a fluid exhauster;
   an exhausting conduit between the fluid exhauster and the guard; and
   exhausting valves configured to control flows of the fluid passing through the exhausting conduit.

11. The immersion exposure system of claim 10, wherein the exhausting conduit comprises:
   a main exhausting conduit connected to the guard;
   a first branch exhausting conduit branching off from the main exhausting conduit and being directly connected to the fluid exhauster; and
   a second branch exhausting conduit provided to connect the main exhausting conduit to the particle counter and to connect the particle counter to the fluid exhauster.

12. The immersion exposure system of claim 11, wherein the exhausting valves comprise:
   a first exhausting valve provided on the first branch exhausting conduit; and
   a second exhausting valve provided on the second branch exhausting conduit.

13. The immersion exposure system of claim 9, wherein the fluid supplying part comprises:
   a fluid source;
   a supplying conduit connecting the fluid source to the guard; and
   a supplying valve configured to control flows of the fluid passing through the supplying conduit.

14. The immersion exposure system of claim 9, further comprising:
   a system control part configured to output an interlock control signal when the particle in the fluid is detected by the particle counter.

15. A particle counter comprising:
   a housing including an inlet, an outlet, and a window between the inlet and the outlet, the housing configured to transport a fluid therethrough from the inlet to the outlet;
   light sources arranged outside the window of the housing, the light sources configured to illuminate the fluid with lights of different wavelengths;
   sensors configured to detect reflections of the lights scattered by at least one of bubbles and particles in the fluid; and
   a control part configured to count the particles by analyzing a difference in intensities of the reflections of the lights, the control part configured to distinguish between the particles and the bubbles, the particles having a varying refractive index, and the bubbles having a constant refractive index.

16. The particle counter of claim 15, wherein the housing further includes a mirror that faces the window.

17. The particle counter of claim 16, wherein the mirror is curved, and a concave portion of the mirror faces the window.

18. The particle counter of claim 15, wherein the light sources are configured such that the lights are incident upon the fluid with a same intensity.

19. The particle counter of claim 15, wherein the light sources and the sensors are aligned such that an illumination direction of the light sources is orthogonal to a detection direction of the sensors.

* * * * *